(12) United States Patent
Morrissette et al.

(10) Patent No.: US 8,383,024 B2
(45) Date of Patent: Feb. 26, 2013

(54) POROUS MATERIAL AND METHOD FOR FABRICATING SAME

(75) Inventors: Daniel Morrissette, Sherbrooke (CA);
Patrick Croteau, Sherbrooke (CA)

(73) Assignee: PPD Meditech (CA)

( * ) Notice: Subject to any disclaimer, the term of this patent is extended or adjusted under 35 U.S.C. 154(b) by 724 days.

(21) Appl. No.: 12/092,487

(22) PCT Filed: Nov. 6, 2006

(86) PCT No.: PCT/CA2006/001808
§ 371 (c)(1),
(2), (4) Date: Nov. 17, 2008

(87) PCT Pub. No.: WO2007/051307
PCT Pub. Date: May 10, 2007

(65) Prior Publication Data
US 2009/0222091 A1    Sep. 3, 2009

Related U.S. Application Data

(60) Provisional application No. 60/733,206, filed on Nov. 4, 2005.

(51) Int. Cl.
*B01D 67/00* (2006.01)
*B29C 44/00* (2006.01)
*B29C 44/60* (2006.01)

(52) U.S. Cl. ............................ 264/48; 264/637; 264/651

(58) Field of Classification Search .................... 521/50, 521/61; 264/48, 53, 637, 621
See application file for complete search history.

(56) References Cited

U.S. PATENT DOCUMENTS

| 3,376,238 | A | | 4/1968 | Gregorian et al. | |
|---|---|---|---|---|---|
| 4,212,839 | A | | 7/1980 | Funahashi | |
| 4,445,951 | A | * | 5/1984 | Lind et al. | 156/93 |
| 5,059,630 | A | * | 10/1991 | Fujita et al. | 521/61 |
| 5,102,917 | A | | 4/1992 | Bedwell et al. | |
| 5,185,111 | A | | 2/1993 | Lazar | |
| 5,205,968 | A | | 4/1993 | Damrow et al. | |
| 5,328,613 | A | | 7/1994 | Beall et al. | |

(Continued)

FOREIGN PATENT DOCUMENTS

| CA | 2 515 682 A1 | 8/2004 |
|---|---|---|
| EP | 1 746 125 A1 | 1/2007 |

(Continued)

OTHER PUBLICATIONS

Polyetherethe Ketone (PEEK) Data Sheet. Steinwall Inc.*

(Continued)

*Primary Examiner* — Randy Gulakowski
*Assistant Examiner* — Kara Boyle

(57) ABSTRACT

A method for fabricating a porous structure from a first material. The method comprises the acts of mixing the first material with a second material to form a mixture, the first material having a melting point which is lower than the second material, heating the mixture under pressure to a temperature between a melting point of the first material and a melting point of the second material, cooling the molten mixture until it hardens and removing the second material from the first material. The method may also include a subsequent annealing step. There is also described a material suitable for implant, illustratively vertebral or spinal implants, comprising a rigid biocompatible polymer such as PEEK comprising a plurality of interconnected pores. The polymer illustratively has a porosity of between 50% and 85% by volume and in a particular embodiment is able to withstand pressures of up to 20 MPa. The porous PEEK material may also have a minimum thickness in any dimension of one (1) inch.

12 Claims, 8 Drawing Sheets

U.S. PATENT DOCUMENTS

| | | | |
|---|---|---|---|
| 5,352,108 A * | 10/1994 | Kagawa et al. | 425/174.4 |
| 5,514,378 A | 5/1996 | Mikos et al. | |
| 6,103,255 A | 8/2000 | Levene et al. | |
| 6,245,537 B1 | 6/2001 | Williams et al. | |
| 2001/0009716 A1 | 7/2001 | Taguchi et al. | |
| 2004/0054021 A1 | 3/2004 | Seargeant | |
| 2008/0032112 A1* | 2/2008 | Hirata et al. | 428/304.4 |

FOREIGN PATENT DOCUMENTS

| | | | |
|---|---|---|---|
| EP | 1746125 | * | 1/2007 |
| EP | 1746125 A1 | * | 1/2007 |
| GB | 1 206 234 A | | 9/1970 |
| GB | 2 232 982 A | | 1/1991 |
| JP | 55-032651 | | 3/1980 |
| JP | 61-185538 | | 8/1986 |
| JP | 63-127749 | | 5/1988 |
| JP | 06-184349 | | 7/1994 |
| JP | 08-198998 | | 8/1996 |
| JP | 2005-046538 | | 2/2005 |
| JP | 2006-028379 | | 2/2006 |
| JP | 2006-057774 | | 3/2006 |
| WO | 2005/103128 A1 | | 11/2005 |
| WO | WO 2005/103128 | * | 11/2005 |
| WO | 206/113984 A1 | | 11/2006 |

OTHER PUBLICATIONS

Polyetherether Ketone (PEEK) Data Sheet, Steinwall Inc. 2007.*

Thomas, R.C. et al., "Hydroxyapatite Fiber Reinforced Poly($\alpha$-hydroxy ester) Foams for Bone Regeneration," *Biomaterials*, 1998, vol. 19, pp. 1935-1943.

Plastics Guide/Molding Processing Edition, Japan, Kogyo Chosakai Publishing Co., Ltd., Nov. 1, 1973, pp. 243 to 247.

* cited by examiner

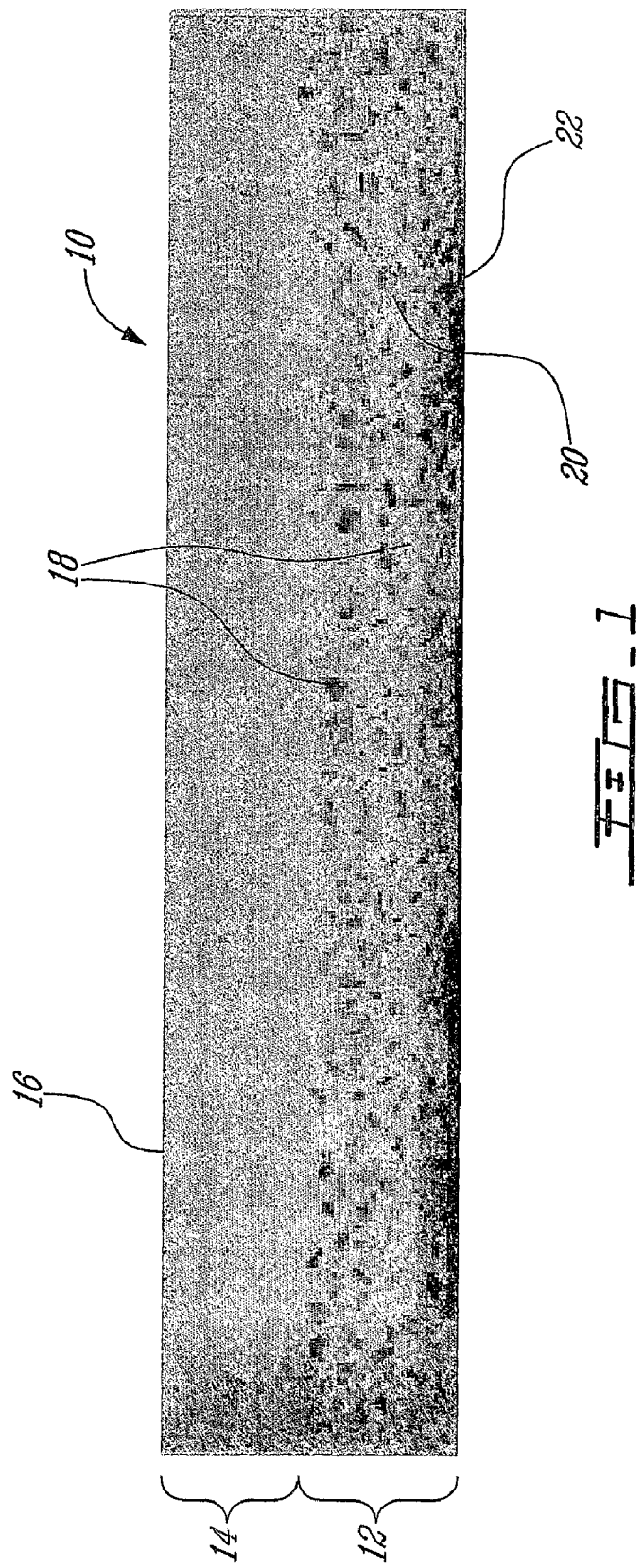

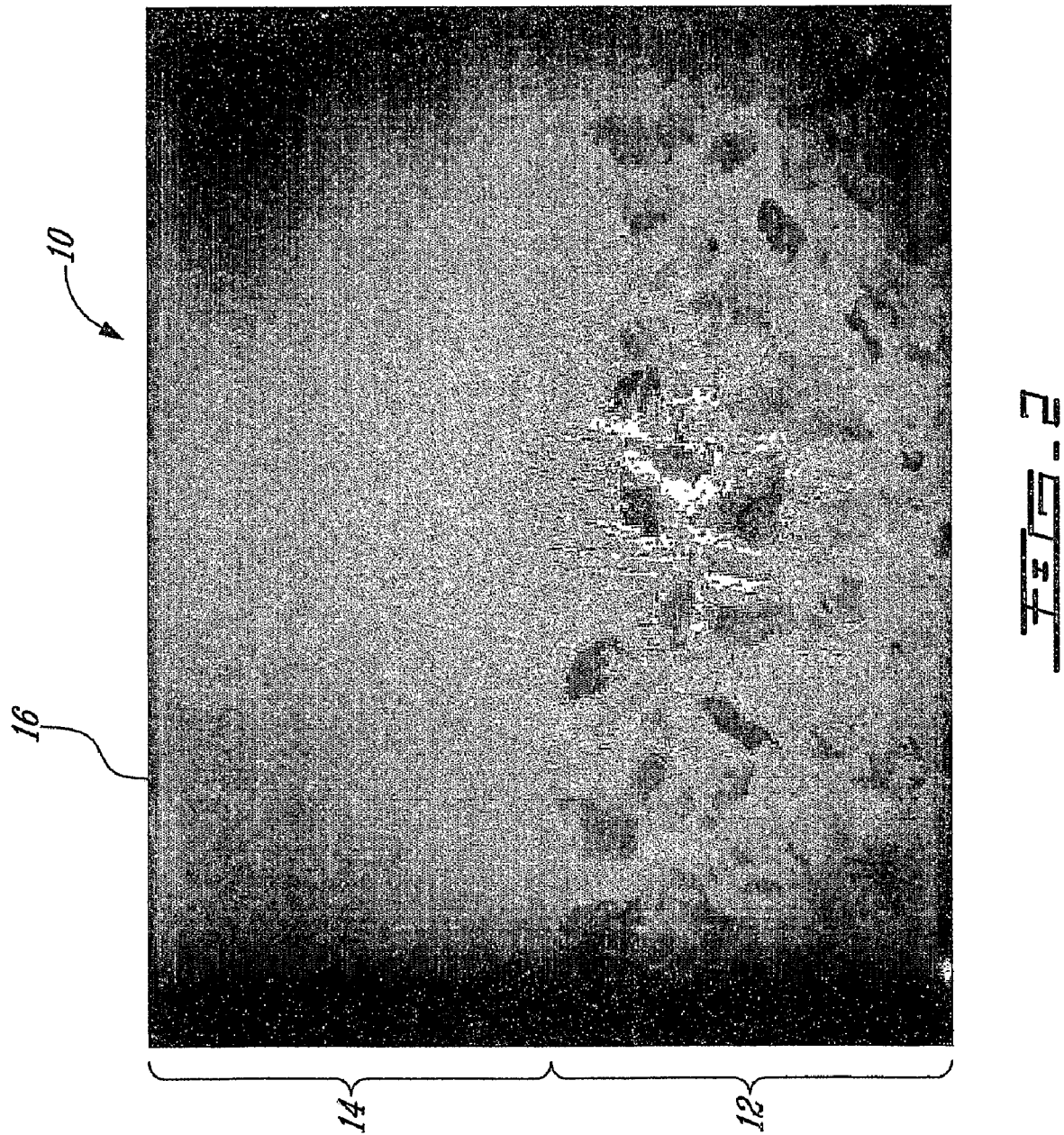

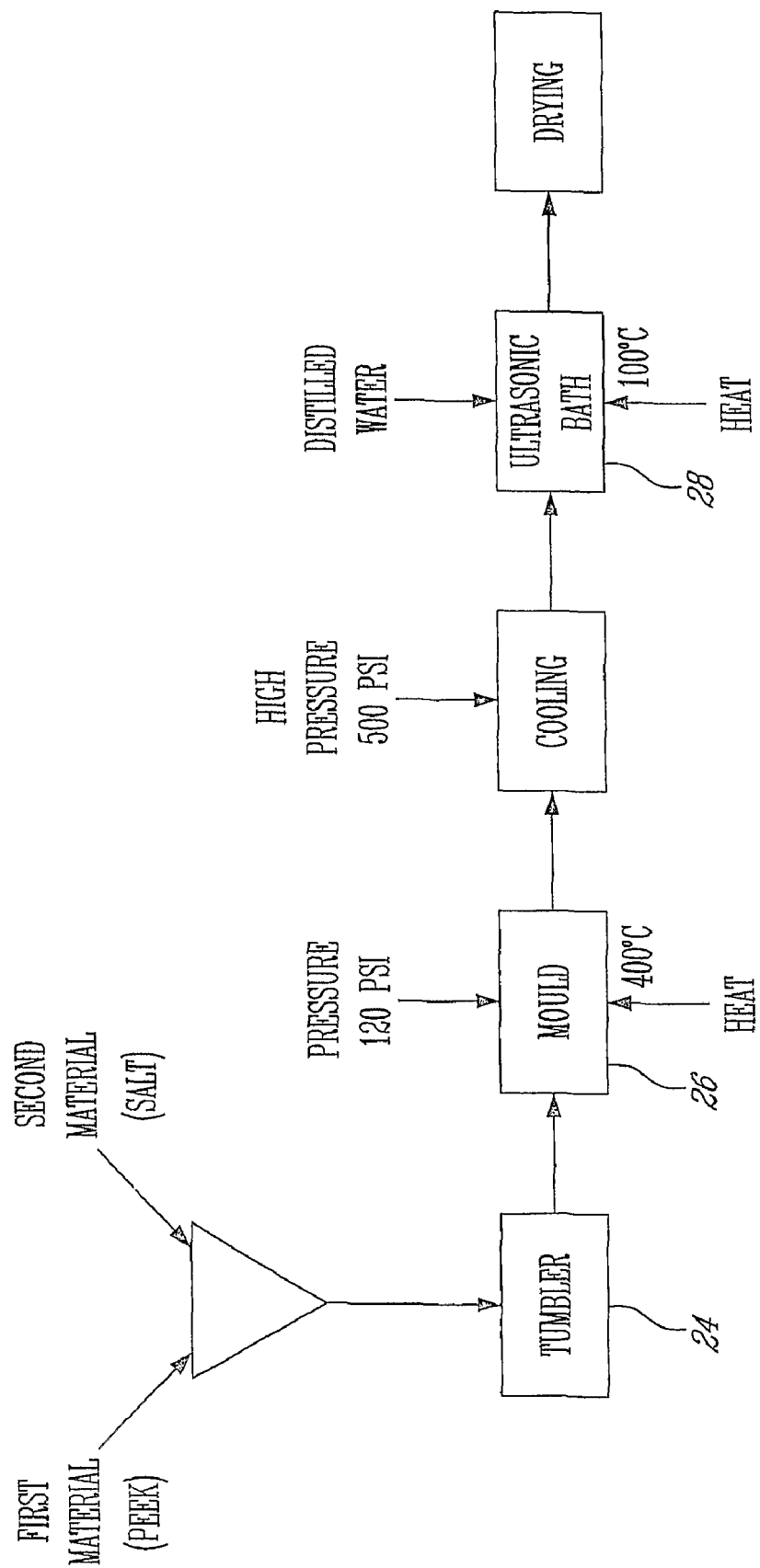

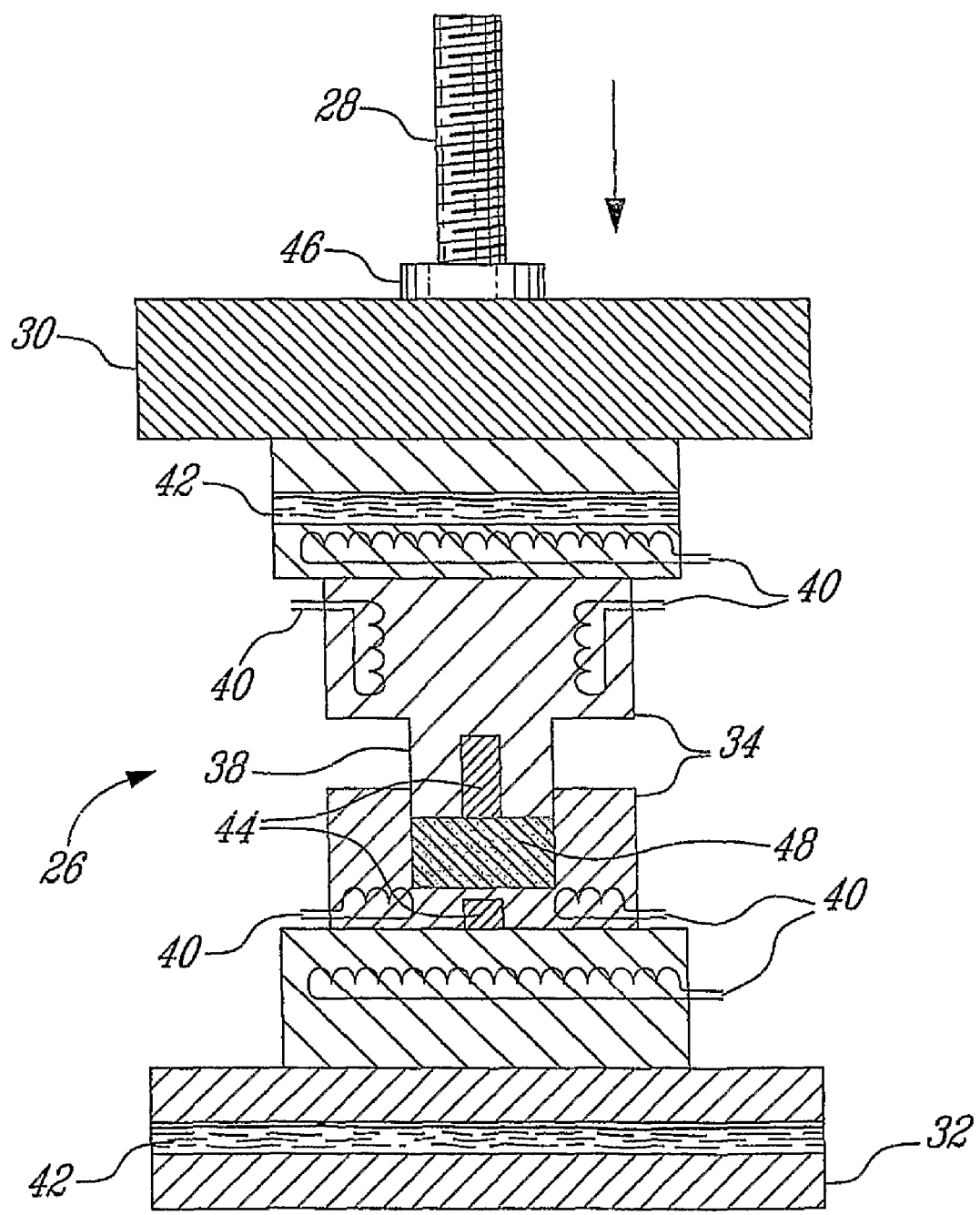
FIG_4B

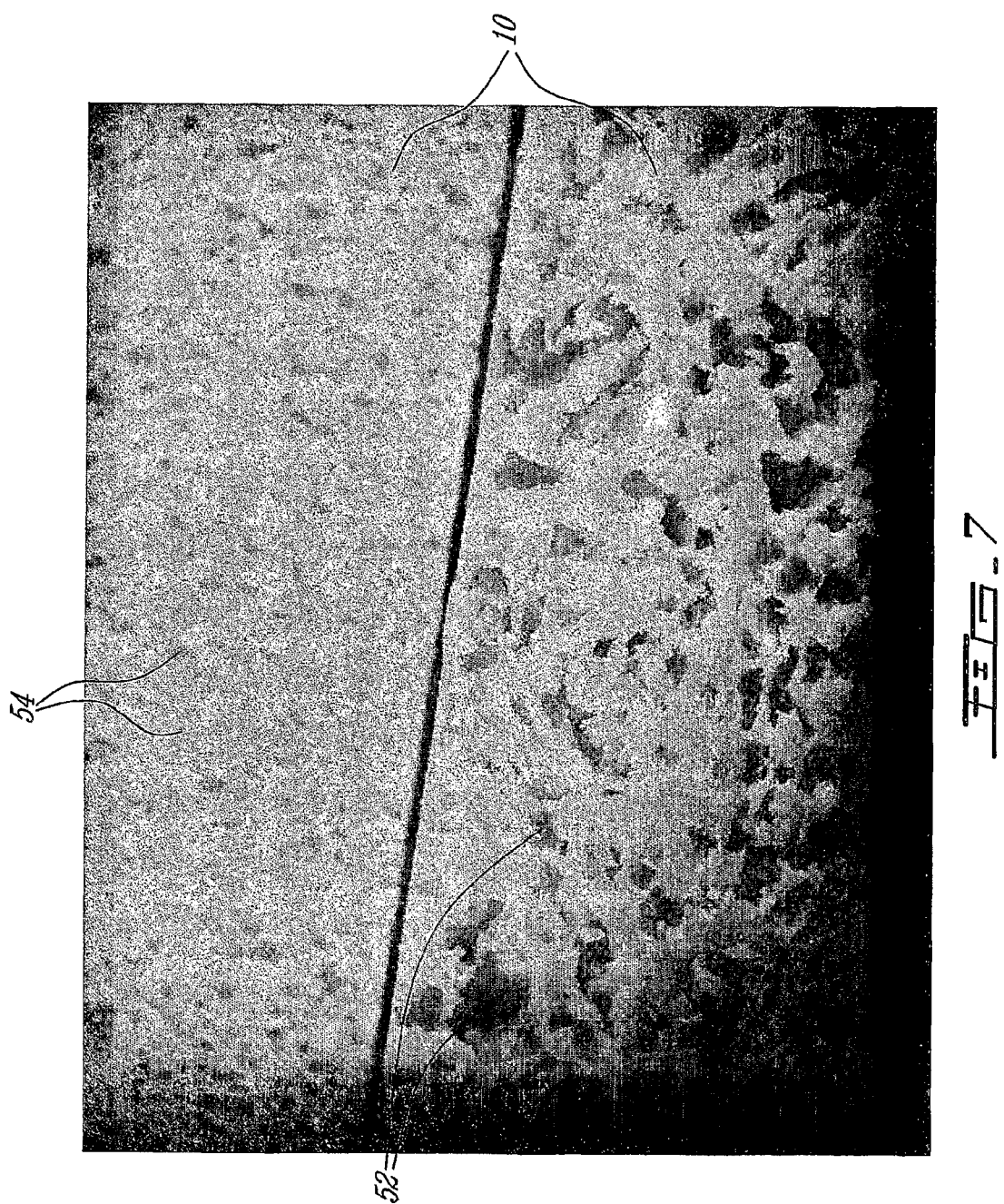

POROUS MATERIAL AND METHOD FOR FABRICATING SAME

CROSS-REFERENCE TO RELATED APPLICATIONS

This application is a §371 of PCT Application No. PCT/CA2006/001808, filed on Nov. 6, 2006 and published in English under PCT Article 21(2) (WO 2007/051307 A2, issued May 10, 2007), which itself claims priority of U.S. Provisional Application No. 60/733,206, filed on Nov. 4, 2005. All documents above are incorporated herein in their entirety by reference.

FIELD OF THE INVENTION

The present invention relates to a porous material and method for fabricating same. In particular, the present invention relates to a porous poly aryl ether ketone such as PEEK fabricated by mixing a dissolvable material with PEEK in a molten form and subsequently removing the dissolvable material. The resultant porous PEEK material is well suited for medical implant devices.

BACKGROUND TO THE INVENTION

A variety of methods exist in the art for forming porous micro-plastic materials. In particular, the prior art discloses producing a porous product by mixing a salt-type pore-forming agent such as sodium chloride to a resin to form a moulding material, subjecting the moulding material to a moulding process to produce a moulded part and subsequently washing the product to elute or leach the salt-type pore forming agent, thereby forming pores. In a particular variant the resin has a lower melting temperature than the salt-type pore-forming agent and the moulding process involves heating the moulding material to a temperature between that of the melting point of the resin and the salt-type pore-forming agent, moulding the product and subsequently cooling the moulded product until it solidifies.

One drawback of such prior art methods is that when forming highly porous materials, a large amount of pore forming agent is required which, given that the pore-forming agent remains in a particulate form, adversely affects the fluidity of the moulding material when using conventional moulding methods. As a result, such desalting methods have proven unsuitable for forming porous materials having 50% or more by volume of pores.

SUMMARY OF THE INVENTION

In order to overcome the above and other drawbacks, there is disclosed a method for fabricating a porous structure from a first material. The method comprises the acts of mixing the first material with a second material to form a mixture, the first material having a melting point which is lower than the second material, heating the mixture under pressure to a temperature between a melting point of the first material and a melting point of the second material, cooling the molten mixture until it hardens and removing the second material from the first material.

There is also disclosed a method for fabricating a porous structure. The method comprises the acts of mixing a fluid material with a solid particulate to form a mixture, hardening the mixture and removing the solid particulate from the hardened mixture.

Additionally, there is disclosed a material suitable for implant comprising a rigid biocompatible polymer comprising a plurality of interconnected pores wherein the polymer has a porosity of between 50% and 85% by volume.

There is also disclosed a composite material comprising a first porous portion comprising a plurality of interconnected pores, a second solid portion having a first surface, the first surface secured to the first portion. The first and second portions are fabricated from the same material.

Furthermore, there is disclosed a material suitable for vertebral implants, comprising a porous biocompatible polymer comprising a plurality of interconnected pores where the polymer can withstand a pressure of up to at least 20 MPa.

Also, there is disclosed a material suitable for implant formed from a porous PEEK polymer comprising a plurality of interconnected pores and having a minimum thickness in any direction of about one (1) inch.

BRIEF DESCRIPTION OF THE FIGURES

FIG. 1 is a cross section of a porous PEEK material in accordance with an illustrative embodiment of the present invention;

FIG. 2 is a detailed cross section of the porous PEEK material in FIG. 1;

FIG. 3 is a schematic diagram of a process to fabricate a porous PEEK material in accordance with an illustrative embodiment of the present invention;

FIGS. 4A and 4B are side cross sectional views of a direct compression moulding setup in accordance with an illustrative embodiment of the present invention;

FIG. 7 is a cross section of two porous PEEK materials fabricated using both coarse and fine particulate.

DETAILED DESCRIPTION OF THE ILLUSTRATIVE EMBODIMENTS

Figure 4A:
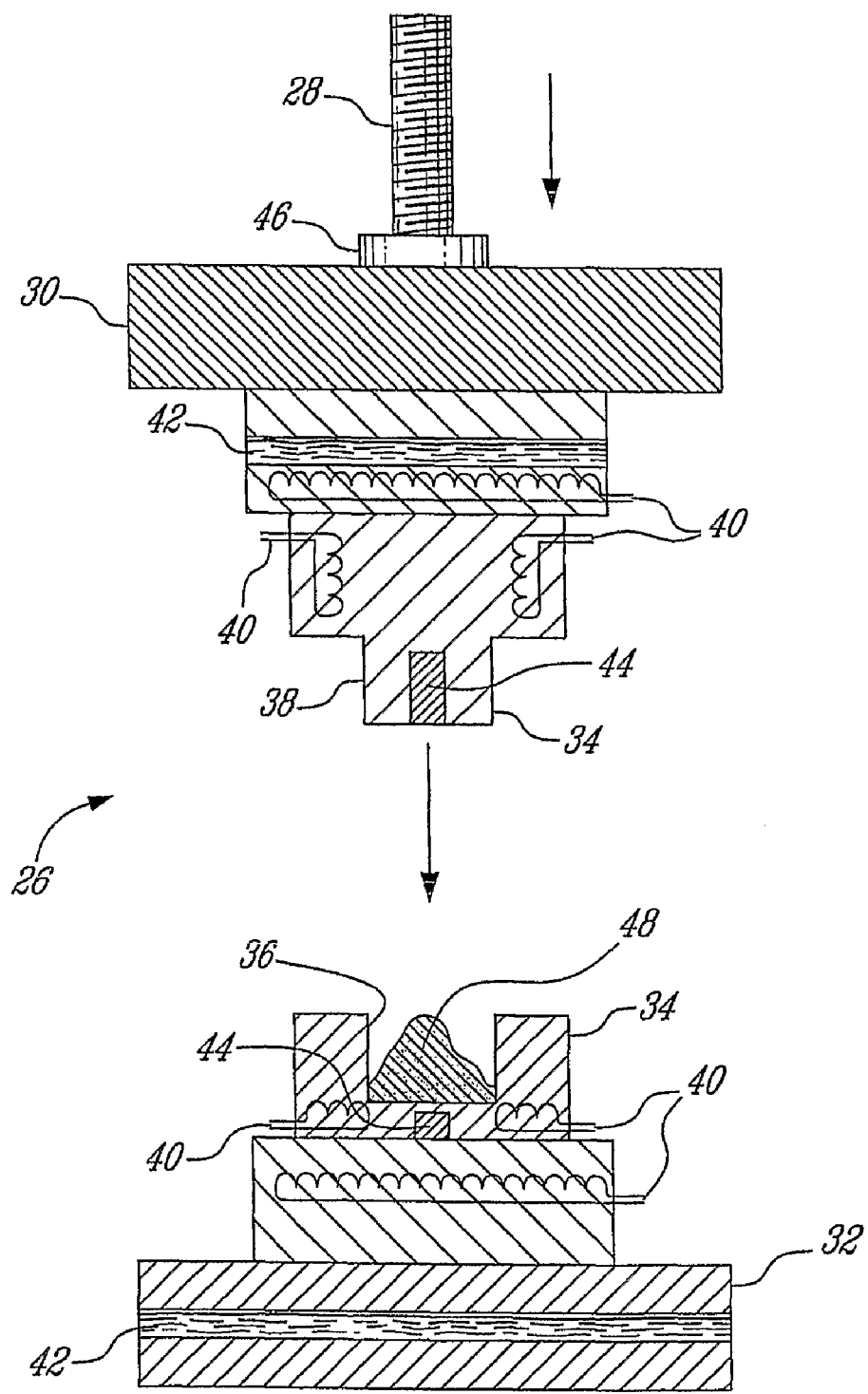

Referring now to FIG. 1, a porous PEEK material, generally referred to using the numeral 10, is disclosed. The porous material is comprised of a porous layer 12 and may also, in a particular embodiment, comprise a non porous layer 14. The non-porous layer may be fabricated together with the porous layer 12 in the same process act or may be subsequently bonded to the porous layer 12. Additionally, a second porous layer may be formed in the upper surface 16 of the non porous layer 14 in the same manner.

Of note is that although the present illustrative embodiment focuses on the use of PEEK as the basic material for fabricating the porous material, other polymers such as PAEK or PEKK could also be used in a particular embodiment.

Referring now to FIG. 2 in addition to FIG. 1, the porous layer 12, is comprised of a series of interconnected pores, or channels, 18 which are visible on both the side face 20 and bottom face 22 of the porous material 10. The interconnection promotes bone in growth which, combined with the inert nature of PEEK, makes the resultant porous composite well suited for implant.

Referring to FIG. 3, in order to fabricate the porous material, a first material, such as PEEK, in the form of flakes or powder, is mixed with a sufficient a mount of a second particulate material which is removable from the first material at a subsequent act to reveal a porous structure. Illustratively, the second material is a dissolvable material, illustratively relatively course table salt (NaCl) having a granule diameter of greater than 180 microns, preferably between about 300 and 710 microns.

In order to ensure that the resulting material is truly porous, the amount of dissolvable material used should be sufficient to form an interconnected structure (or interconnected passageways) once the material has been removed, which will depend to some degree on the distribution of granule size as well as the relative amounts. Illustratively, 20% PEEK by weight is placed along with 80% course table salt by weight in a tumbler 24 and the mixture tumbled for ten (10) minutes at medium speed. Following mixing, the PEEK/salt admixture is placed in a mould assembly 26.

Referring now to FIGS. 4A and 4B, the mould assembly 26 is illustratively comprised of a piston 28 which drives a moveable upper platen 30 towards a fixed lower platen 32. A mould 34 comprised of a mould cavity 36 and a mould cap 38 which fits snugly within the mould cavity 36. Controlled heating of the mould cavity 36 and the mould cap 38 is provided for example via a plurality of electrical heating elements as in 40. Additionally, controlled cooling of the mould cavity 36 and the mould cap 38 is provided for example through cavities as in 42 in both the upper platen 30 and the lower platen 32 through which a cooling fluid such as water may be circulated. Temperatures of the material within the mould cavity 36 are detected via thermo couples as in 44 mounted proximate to the lower end of the mould cavity 36 and the mould cavity 36. Furthermore, the actual pressure applied between the platens 30, 32 by the piston 28 can be detected by means of a load cell 46. Provision of independent heating elements as in 40 and cooling cavities 42 as well as he provision of a plurality of thermo couples 44 means that the upper platen 30, and thus the mould cap 38, can be heated and cooled independently of the lower platen 32, and thus the mould cavity 36, which ensures accurate control of the temperature of the admixture 48 within the mould 34.

Although the piston 28 is preferably driven by an electric actuator (not shown), other types of actuators, such as hydraulic or compressed air may also be suitable in certain applications. Additionally, although heating and cooling of the platens 30, 32 is described as illustratively being provided by respectively electrical heating and water cooling, other means of heating and cooling the mould 34 (such as Peltier effect devices or the like) may be provided for with appropriate modifications to the assembly 26.

Referring back to FIG. 3 in addition to FIG. 4A, as discussed above, the PEEK/salt admixture 48 is placed in a mould cavity 36. Referring now to FIG. 4B, the ram 28 is actuated such that the upper platen 30 is lowered towards the lower platen 32 and the mould cap 38 is inserted into the mould cavity 36. Of note is that the mould cap 38 and mould cavity 36 may take on any number of simple or complex forms, thereby allowing materials to be formed for subsequent machining or parts with a variety of moulded shapes.

Figure 5:
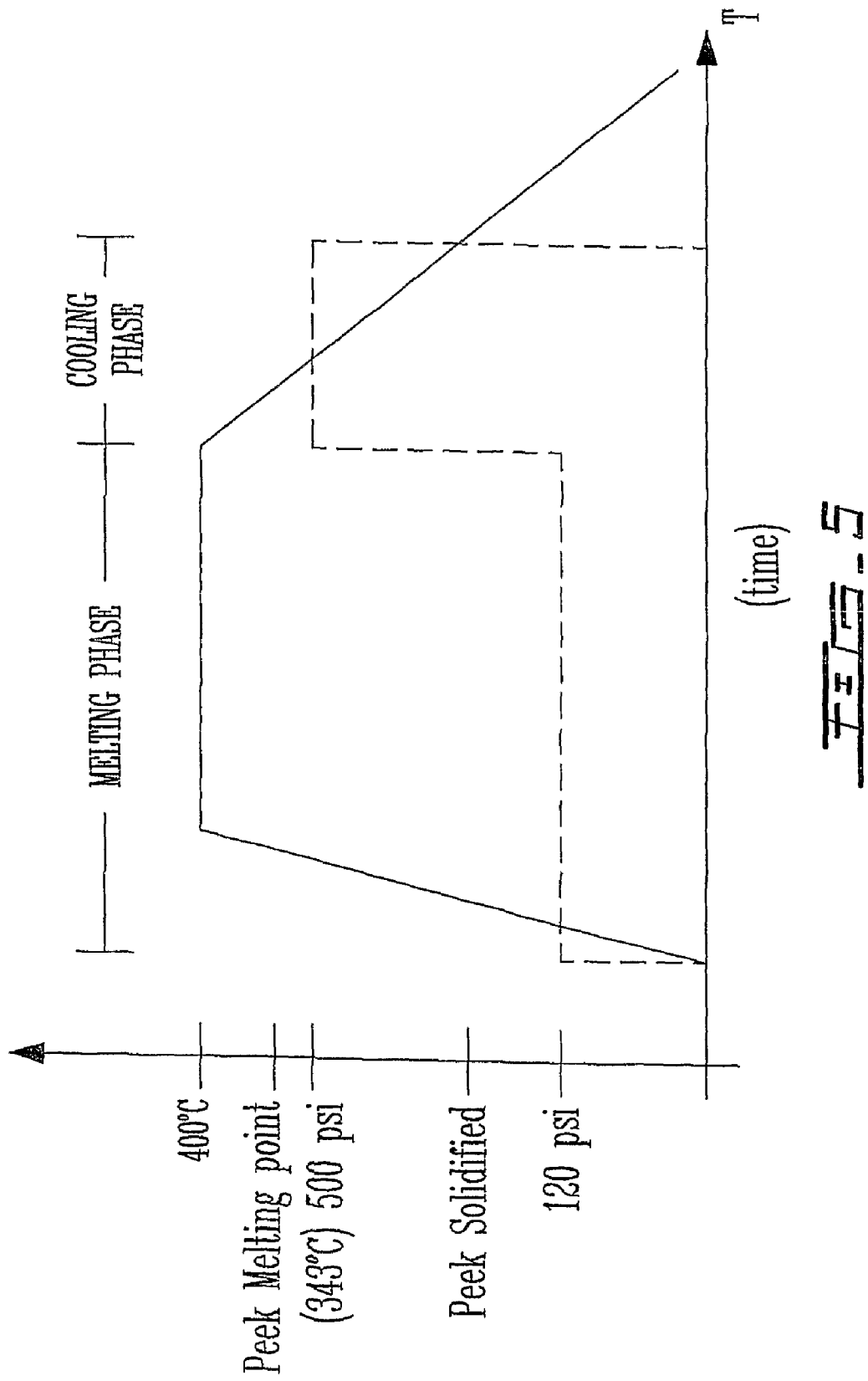
FIG. 5 is a graph of the pressure and temperature versus time of a process to fabricate a porous PEEK material in accordance with an illustrative embodiment of the present invention

Referring now to FIG. 5 in addition to FIG. 4B, during the melting phase (as labelled on FIG. 5) current is applied to the electrical heating elements 40 in order to heat mould 34 thus melting the admixture 48 while a constant low pressure is applied to the admixture 48 by the ram 28. As the melting temperature of PEEK is bout 355° C., the admixture 48 is illustratively heated to about 400° C., which is above the melting point of PEEK yet far below the melting point of salt. Additionally, a constant low pressure of about 120 psi pressure is applied to the admixture 48 by the ram 28. The duration of the melting phase is dependant on a number of factors including the amount of admixture 48 within the mould 34 but is at least long enough to ensure that all the first material (in this case the PEEK) has melted. At the end of the melting phase the electrical heating elements 40 are deactivated and the cooling phase entered.

Still referring to FIG. 5, during the cooling phase a high pressure of illustratively about 500 psi is applied by the ram 28 to the admixture 48 and water (or other cooling fluid) circulated within the cavities 42 thereby cooling the mould 34 and the admixture 48 contained within the mould. Note that although the graph indicates that cooling of the mould is linear, other cooling, such as step wise cooling, could also be carried out.

One advantage of heating and cooling the admixture 48 in this fashion while under pressure is that it provides for a better positioning of the molecular chains within the resultant moulded material. Indeed, no alignment of the molecular chains of the material is provoked and the resultant moulded material displays advantageous multidirectional mechanical properties. Additionally, application of pressure during heating and subsequent cooling in this fashion prevents air bubbles from forming within the molecular chains, thereby allowing relatively large porous parts, that is in excess of one (1) inch in all dimensions, to be formed.

Once the admixture 48 has adequately solidified, the ram 28 is actuated to retract the mould cap 38 from the mould cavity 36 thereby allowing the moulded admixture 48 to be removed from the mould cavity 36.

The solidified moulded admixture 48 is subsequently placed in an ultrasonic bath 28 containing heated distilled water. Illustratively, the water is heated to 100° C. The solidified moulded admixture 48 is soaked in the bath until the salt has been dissolved from the part, thereby revealing the interconnected pores, illustratively for 16 hours. The porous part is then removed from the bath 28 and allowed to dry, illustratively for 24 hours.

In order to improve the strength of the yielded porous part annealing techniques can be used. Typically, the annealing techniques used are supplied by the manufacturer of the raw materials. In the present illustrative embodiment, the porous parts were placed in an annealing oven and allowed to dry for a minimum of three (3) hours at 150° C. The parts were then subject to heat increasing at a rate of 10° C. per hour until a temperature of 250° C. was reached. The parts were held at this temperature for an amount of time dependant on the thickness of the part, but at least four (4) hours. The parts were then cooled at a rate of −10° C. per hour until 140° C. is reached, at which point the annealing oven was turned off and the part allowed to return to room temperature.

Figure 6:
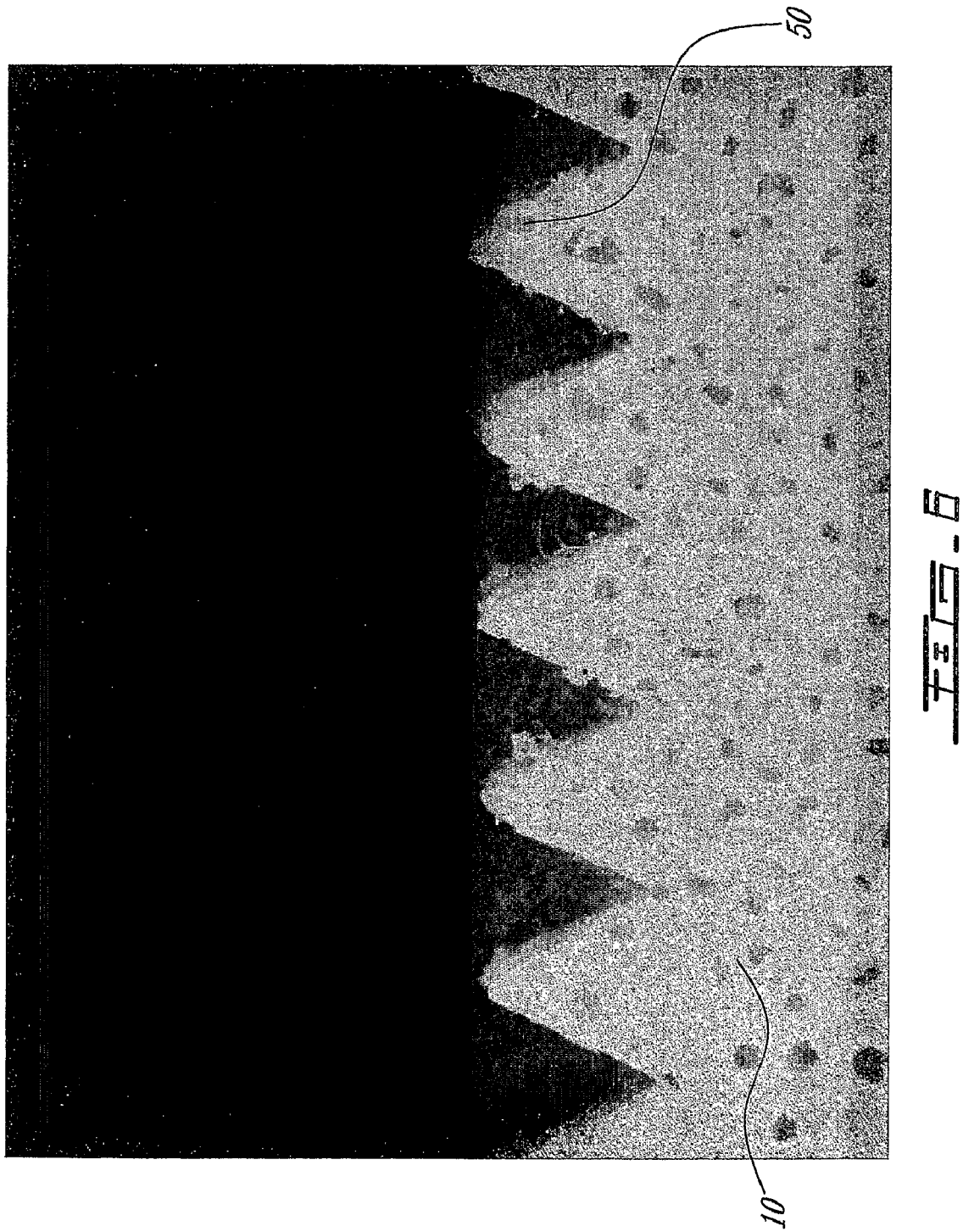
FIG. 6 is a cross section of a machined porous PEEK material in accordance with an illustrative embodiment of the present invention.

The resultant porous PEEK material is suitable for implant, with the interconnected pores promoting bone in growth. Additionally, PEEK lends itself well to machining allowing porous PEEK parts such as those fabricated according to the present invention to be shaped using a variety of cutting tools. Referring to FIG. 6, an example of porous PEEK material 10 with a serrated edge 50 (also known as Spine Cage Teeth) machined therein and suitable, for example, for orthopaedic implant is shown.

Additionally, referring to FIG. 7, by using a coarser or finer second particulate material, porous PEEK material 10 having larger pores as in 52 or smaller pores as in 54 may be achieved.

A series of five (5) test parts were fabricated using an admixture of PEEK and salt and according to the above process. The test parts where all of cylindrical shape and having the following dimensions:

| | |
|---|---|
| Diameter | 0.400 inch |
| Height | 0.460 inch |
| Surface Area | 0.126 inch² |

Additionally, the average size of the salt grains was varied in order to yield parts having different typical pore sizes. The test parts were subject to a compression test on a conventional compression testing machine. The tests each comprised placing a part between upper and lower plates and subjecting the part to an increasing pressure until it collapsed. The results of this analysis are tabled below in TABLE 1.

TABLE 1

| Sample # | Porosity (% by volume) | Pore diameter (microns) | Maximum Sustainable Pressure (MPa) |
|---|---|---|---|
| 1 | 70 | 300 to 410 | 17.68 |
| 2 | 70 | 410 to 500 | 18.27 |
| 3 | 70 | 500 to 710 | 21.7 |
| 4 | 60 | 300 to 410 | 40.59 |
| 5 | 80 | 300 to 410 | 7.77 |

In general, and as would be expected, it can be said that as % porosity by weight increases, overall strength is reduced. Additionally, referring to samples 1 through 3 it is apparent that an increased typical pore size leads to a material which is more able to withstand pressure. For example, in order for a part to be suitable for implant in the vertebral column it must be able to withstand pressures of at least 20 Megapascals (Mpa), which is achieved by samples 3 and 4 but not samples 1, 2 and 5.

In an alternative embodiment pure PEEK can be placed in the bottom of the mould, or on top of the PEEK/salt admixture, in order to form a solid PEEK/porous PEEK composite. The solid layer acts as a barrier between the porous layer and other parts and may be used, for example, to limit bone in growth into the resultant moulded part. Additionally, as discussed above PEEK lends itself well to machining, and as a result the solid layer can be machined, for example for interconnection with other parts fabricated from PEEK or other materials, such as titanium, tantalum or the like. Alternatively, other PEEK composite materials such as PEEK reinforced with carbon (e.g. PEEK carbon prepreg or pre-impregnated fibres) or other fibres can be moulded together with the PEEK/salt admixture to provide composite structures having a variety of different characteristics in terms of strength, stiffness, flexibility and the like, thereby making the resultant composite suitable for a wide variety of applications.

Additionally, a multilayered solid/porous composite can be formed by alternating layers of PEEK or PEEK composites and Peek/salt mixture.

In another alternative illustrative embodiment the method of the present invention can be applied more generally using materials other than PEEK and table salt. Indeed, as will now be understood by persons of ordinary skill in the art, the present invention can be applied to virtually any first material which is in a liquid or fluid form at a temperature below the melting point of the second particulate material and which is subsequently able to harden to form a solid composite. Of course, the second particulate material must also be able to be removed from the solid composite to leave the porous structure of the hardened first material.

In still another alternative illustrative embodiment the method of the present invention can be applied more generally to a first material in a liquid form at room temperature, such as an epoxy or other polymer, which subsequently hardens following mixing with a second solid particulate material through the introduction of a catalyst hardener or the like. A similar result can be arrived at with first materials which may be heat set, or cured, through the application of heat and pressure.

Although the present invention has been described hereinabove by way of an illustrative embodiment thereof, this embodiment can be modified at will, within the scope of the present invention, without departing from the spirit and nature of the subject of the present invention.

What is claimed is:

1. A method for fabricating a porous structure from a polymer, the method comprising:
   mixing the polymer with a particulate material to form a mixture, the polymer having a melting point which is lower than said particulate material;
   heating said mixture under a first pressure of from 100 psi to 200 psi to a temperature between a melting point of the polymer and a melting point of said particulate material;
   cooling said molten mixture under a second pressure greater than said first pressure until it hardens; and
   removing said particulate material from the polymer;
   wherein an amount of said particulate material relative to the polymer is present such that removal of said particulate material from said hardened mixture leaves a resultant structure comprised of the polymer and a plurality of interconnected passageways.

2. The method of claim 1, wherein said second pressure is greater than about 500 psi.

3. The method of claim 1, wherein the polymer is a poly aryl ether ketone.

4. The method of claim 1, wherein said poly aryl ether ketone is PEEK, said particulate material is table salt and said temperature between 390° C. and 410° C., preferably 400° C.

5. The method of claim 1, wherein the polymer is in particulate form and said mixing act comprises placing the polymer and said particulate material in a tumbler and rotating said tumbler.

6. The method of claim 3, wherein said heating act comprises heating said mixture to about 400° C.

7. The method of claim 1, wherein an amount of said particulate material relative to the polymer is present such that removal of said particulate material from said hardened mixture leaves a resultant structure comprised of the polymer and a plurality of interconnected passageways.

8. The method of claim 7, wherein said mixture comprises 20% by weight of the polymer and 80% by weight of said particulate material.

9. The method of claim 1, wherein said particulate material is dissolvable in a solvent which does not react with the polymer and said removing act comprises washing said hardened molten mixture in a bath of said solvent.

10. The method of claim 9, wherein said particulate material is table salt and said solvent is water.

11. The method of claim 10, wherein said table salt is comprised of salt particles having a size of greater than 180 microns.

12. The method of claim 1, further comprising the act, following said removing act, of annealing the porous structure.

* * * * *